United States Patent
Li (10) Patent No.: US 12,226,261 B2
(45) Date of Patent: Feb. 18, 2025

(54) ULTRASOUND TRANSIENT ELASTICITY MEASUREMENT DEVICE AND METHOD

(71) Applicant: SHENZHEN MINDRAY BIO-MEDICAL ELECTRONICS CO., LTD., Guangdong (CN)

(72) Inventor: Shuangshuang Li, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 0 days.

(21) Appl. No.: 17/082,822

(22) Filed: Oct. 28, 2020

(65) Prior Publication Data
US 2021/0038195 A1     Feb. 11, 2021

Related U.S. Application Data

(63) Continuation of application No. PCT/CN2018/085180, filed on Apr. 28, 2018.

(51) Int. Cl.
A61B 8/08    (2006.01)
A61B 8/00    (2006.01)

(52) U.S. Cl.
CPC ............ *A61B 8/485* (2013.01); *A61B 8/4444* (2013.01); *A61B 8/461* (2013.01); *A61B 8/5246* (2013.01); *A61B 2562/0247* (2013.01)

(58) Field of Classification Search
CPC ....... A61B 8/485; A61B 8/4444; A61B 8/461; A61B 8/5246; A61B 2562/0247
See application file for complete search history.

(56) References Cited

U.S. PATENT DOCUMENTS 6,077,226 A * 6/2000 Washburn ............... A61B 8/461
600/443
8,147,410 B2    4/2012 Zheng
(Continued)

FOREIGN PATENT DOCUMENTS

CN    101843501 A    9/2010
CN    102469989 A    5/2012
(Continued)

OTHER PUBLICATIONS

Translated Diao CN106037816A (Year: 2016).*
(Continued)

*Primary Examiner* — Joel Lamprecht
*Assistant Examiner* — Brooke Lyn Klein
(74) *Attorney, Agent, or Firm* — Sheppard Mullin Richter & Hampton LLP (57) ABSTRACT

An ultrasound transient elasticity measurement device and a transient elasticity measurement method are provided. The device includes an ultrasound probe including a vibrator, a transmitting/receiving sequence controller, and a data processor. The method includes: transmitting a first ultrasound wave according to a first transmitting/receiving control sequence, and receiving an echo thereof; generating an ultrasound image according to the echo of the first ultrasound wave, and displaying the same; detecting a region of interest on the ultrasound image selected by a user; a vibrator driving the ultrasound probe to vibrate; transmitting a second ultrasound wave according to a second transmitting/receiving control sequence, and receiving an echo thereof, the second transmitting/receiving control sequence being determined according to the region of interest on the ultrasound image selected by the user; and calculating, according to the echo of the second ultrasound wave, the transient elasticity result of the region of interest.

15 Claims, 6 Drawing Sheets

(56) References Cited

U.S. PATENT DOCUMENTS

| | | | |
|---|---|---|---|
| 8,469,891 B2 | 6/2013 | Maleke et al. | |
| 2008/0269606 A1* | 10/2008 | Matsumura | A61B 8/12 |
| | | | 600/438 |
| 2012/0123263 A1 | 5/2012 | Osaka et al. | |
| 2015/0133782 A1* | 5/2015 | Yoshikawa | A61B 8/485 |
| | | | 600/438 |
| 2016/0143621 A1 | 5/2016 | Parthasarathy et al. | |
| 2016/0143625 A1* | 5/2016 | Shikata | A61B 8/4477 |
| | | | 600/459 |
| 2016/0249884 A1* | 9/2016 | Hashimoto | A61B 8/485 |
| | | | 600/438 |
| 2016/0317128 A1* | 11/2016 | Sakaguchi | G16H 50/30 |
| 2018/0025492 A1* | 1/2018 | Honjo | A61B 5/7271 |
| | | | 382/128 |
| 2018/0055479 A1 | 3/2018 | Lalena | |
| 2018/0368808 A1* | 12/2018 | Wang | A61B 8/00 |

FOREIGN PATENT DOCUMENTS

| | | |
|---|---|---|
| CN | 102641137 A | 8/2012 |
| CN | 105395218 A | 3/2016 |
| CN | 105491959 A | 4/2016 |
| CN | 106037816 A * | 10/2016 |
| JP | 2013244162 A * | 12/2013 |

OTHER PUBLICATIONS

Translated Tanabe JP2013244162 (Year: 2013).*
PCT International Search Report and the Written Opinion mailed Dec. 19, 2018, issued in related International Application No. PCT/CN2018/085180, with partial English translation (8 pages).
First Search dated Sep. 17, 2020, issued in related Chinese Application No. 201880018259.5 (1 page).
First Office Action dated Sep. 27, 2020, issued in related Chinese Application No. 201880018259.5, with English machine translation (15 pages).
PCT International Preliminary Report on Patentability mailed Nov. 12, 2020, issued in related International Application No. PCT/CN2018/085180, with English translation (10 pages).
Supplementary Search dated Jan. 21, 2021, issued in related Chinese Application No. 201880018259.5 (1 page).

* cited by examiner

ULTRASOUND TRANSIENT ELASTICITY MEASUREMENT DEVICE AND METHOD

CROSS-REFERENCE TO RELATED APPLICATION

This application is a continuation application of International Patent Application No. PCT/CN2018/085180, filed with the China National Intellectual Property Administration (CNIPA) of People's Republic of China on Apr. 28, 2018, and entitled "ULTRASOUND-BASED TRANSIENT ELASTICITY MEASUREMENT DEVICE AND METHOD". The entire content of the above-identified application is incorporated herein by reference.

TECHNICAL FIELD

The present disclosure relates to medical device, in particular to a transient elasticity measurement device.

BACKGROUND

Ultrasound transient elasticity measurement mainly represents the elasticity or softness of tissues through non-invasive detection methods, and is widely used by doctors in the auxiliary diagnosis of clinical liver diseases (especially the degree of liver fibrosis).

In the transient elasticity measurement methods, the external vibration may be used to generate the shear waves propagating in the tissue. The ultrasound waves may be used to detect the shear wave, so as to calculate the elasticity of the tissue and provide the quantitative measurement results, thereby facilitating the doctor to make an objective diagnosis.

However, since it is difficult for the shear wave to propagate in blood vessels, if the propagation path passes through the blood vessels or the liquid tumors, etc., the quality of the elasticity measurement will be significantly affected. However, the conventional transient elasticity measurement system can only provide the information of M image, by which the structure and shape of the tissue being examined cannot be intuitively observed and invalid or wrong measurements are not easy to be avoided.

SUMMARY

In one embodiment, an ultrasound transient elasticity measurement device is provided, which may include:
  an ultrasound probe including a vibrator and a transducer, where, the vibrator is configured to drive the transducer to vibrate so as to generate a shear wave that propagates to inside of a biological tissue, the transducer includes multiple elements, and at least part of the multiple elements are configured to transmit a first ultrasound wave to the biological tissue before the transducer vibrates and receive echoes of the first ultrasound wave returned from the biological tissue to obtain echo data of the first ultrasound wave, and to transmit a second ultrasound wave to a region of interest in the biological tissue after the transducer vibrates and receive echoes of the second ultrasound wave returned from the biological tissue to obtain echo data of the second ultrasound wave;
  a transmitting/receiving sequence controller configured to output a first transmitting/receiving control sequence to the transducer before the transducer vibrates to control the transducer to transmit the first ultrasound wave and receive the echoes of the first ultrasound wave and output a second transmitting/receiving control sequence to the transducer after the transducer vibrates to control the transducer to transmit the second ultrasound wave and receive the echoes of the second ultrasound wave, wherein, the first transmitting/receiving control sequence is for the purpose of obtaining an ultrasound image, the second transmitting/receiving control sequence is for the purpose of obtaining a transient elasticity result of the region of interest, and the second transmitting/receiving control sequence is determined according to the region of interest selected by a user on the ultrasound image;
  a data processor configured to generate an ultrasound image data according to the echo data of the first ultrasound wave and calculate a transient elasticity result of the region of interest according to the echo data of the second ultrasound wave; and a human-computer interaction device configured to display an ultrasound image on a display interface according to the ultrasound image data, determine the region of interest selected by the user on the ultrasound image, and display the transient elasticity result.

In one embodiment, an ultrasound transient elasticity measurement method is provided, which may include:
  outputting a first transmitting/receiving control sequence a transducer of an ultrasound probe to control the transducer to transmit a first ultrasound wave to a biological tissue and receive echoes of the first ultrasound wave returned from the biological tissue to obtain an echo data of the first ultrasound wave, where the first transmitting/receiving control sequence is for the purpose of obtaining an ultrasound image;
generating an ultrasound image according to the echo data of the first ultrasound wave, and displaying the ultrasound image;
  determining a region of interest selected by a user on the ultrasound image; generating a second transmitting/receiving control sequence according to the region of interest, where the second transmitting/receiving control sequence is for the purpose of obtaining a transient elasticity result of the region of interest;
  a vibrator driving the transducer to vibrate after the region of interest is determined;
  outputting the second transmitting/receiving control sequence to the transducer after the vibrator vibrates to control the transducer to transmit a second ultrasound wave to the region of interest and receive echoes of the second ultrasound wave to obtain an echo data of the second ultrasound wave; and
  calculating a transient elasticity result of the region of interest according to the echo data of the second ultrasound wave.

In the embodiments of the present disclosure, because the ultrasound imaging may be performed to obtain the ultrasound image before the transient elasticity detection is performed, the user can determine the region of interest under the guidance of the ultrasound image, thereby avoiding the region that forms an obstacle to the shear wave and improving the accuracy of transient elasticity detection results.

DETAILED DESCRIPTION

The present disclosure will be described in detail below with reference to the embodiments and drawings, where similar elements in different embodiments are designated with similar reference numbers. In the following embodiments, many details are described so as to facilitate the understanding to the present disclosure. However, those skilled in the art will easily recognize that some of the features may be omitted in different situations, or may be replaced by other elements, materials or methods. In some cases, some operations are not shown or described in the specification, which is to avoid the core part of the present disclosure being overwhelmed by too many descriptions. For those skilled in the art, detailed description of these operations is not necessary. They can fully understand these operations according to the description in the specification and general technical knowledge in the field.

In addition, the features, operations or characteristics described in the specification may be combined in any appropriate manner to form various embodiments. Furthermore, the steps or actions in the described methods may also be changed or adjusted in the order in a manner obvious to those skilled in the art. Therefore, the various orders in the description and drawings are only for clearly describing a certain embodiment, but not meant to be a necessary order unless otherwise stated that a certain order must be followed.

The serial numbers for the elements in the present disclosure, such as "first", "second", etc., are only used to distinguish the described objects, but do not have any order or technical meaning. The "connection" and "coupling" as used herein, unless otherwise specified, will include both direct and indirect connection (coupling).

The concept of the present disclosure is using the same ultrasound probe to obtain B-mode or C-mode image first such that the user can conveniently observe the structure or blood flow information of the target tissue and adjust the position where the transient elasticity measurement will be performed according to the presentation of the ultrasound image, and then perform the transient elasticity measurement, thereby improving the accuracy of transient elasticity measurement.

Figure 1:
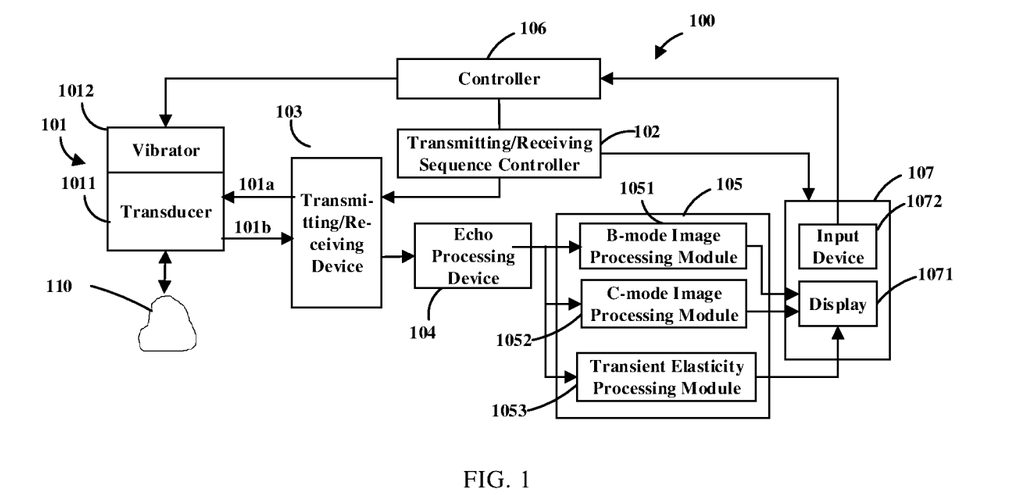
FIG. 1 is a schematic block diagram of an ultrasound transient elasticity measurement device in one embodiment.

In one embodiment of the present disclosure, the transient elasticity measurement device may be an ultrasound image device. Referring to FIG. 1, the ultrasound transient elasticity measurement device 100 may include an ultrasound probe 101, a transmitting/receiving sequence controller 102, an echo processing device 104, a data processor 105, a human-computer interaction device 107 and a controller 106. The transmitting/receiving sequence controller 102 may be connected to the ultrasound probe 101 through a transmitting/receiving device 103. The ultrasound probe 101 may be connected to the echo processing device 104 through the transmitting/receiving device 103. The output end of the echo processing device 104 may be connected to the data processor 105. The output end of the data processor 105 may be connected to the human-computer interaction device 107. The ultrasound probe 101 may include a transducer 1011 and a vibrator 1012. The controller 106 may be connected to the human-computer interaction device 107 and the vibrator 1012, respectively.

The vibrator 1012 may be mounted on the ultrasound probe 101, such as on the housing of the ultrasound probe 101. Alternatively, the vibrator 1012 may be mounted in the housing of the ultrasound probe 101 so as to be assembled with the transducer and other probe components into an integrated ultrasound probe. The vibrator may drive the transducer to vibrate. For example, the vibrator itself may vibrate according to a vibration control sequence so as to drive the transducer to vibrate. Alternatively, the vibrator itself may not vibrate, while the telescopic or rotating part thereof moves so as to drive the transducer to vibrate. The vibration may cause the deformation of the biological tissue when the ultrasound probe contacts the biological tissue, and generate a shear wave that propagates to inside of the biological tissue.

The transducer 1011 may include multiple elements arranged in an array. The multiple elements may be arranged in a row to form a linear array, or arranged in a two-dimensional matrix to form a matrix array. The multiple elements may also form a convex array. The elements may transmit ultrasound waves according to the excitation electrical signal, or transform the received ultrasound waves into electrical signals. Therefore, the element may be used for transmitting the ultrasound waves to the biological tissue in the region of interest, and may also be used for receiving the ultrasound echoes returned from the tissue. When performing the ultrasound testing, it may be controlled by the transmitting control sequence and the receiving control signals which elements will be used in the transmitting of the ultrasound waves and which elements will be used in the receiving of the ultrasound echoes. Alternatively, the element may be controlled to both transmit the ultrasound waves and receive the ultrasound echoes in a time division manner. The elements participating in the ultrasound transmitting may be excited by the electrical signals at the same time, so as to transmit the ultrasound waves at the same time. Alternatively, the elements participating in the ultrasound transmitting may be excited by the electrical signals with a certain time interval, so as to continuously transmit the ultrasound waves with a certain time interval.

The transmitting/receiving sequence controller 102 may generate the transmitting control sequence and the receiving control sequence. The transmitting control sequence may control part or all of the multiple elements to transmit the ultrasound waves to the biological tissue. The parameter of the transmitting control sequence may include the positions of the elements participating in the transmitting, the number of the elements participating in the transmitting and the ultrasound transmitting parameters (such as the amplitude, frequency, number of transmitting, interval of transmitting, angle of transmitting, wave type, focus position, etc.). The receiving control sequence may control part or all of the multiple elements to receive the echoes of the ultrasound wave returned from the tissue. The parameter of the receiving control sequence may include the positions of the elements participating in the receiving, the number of the elements participating in the receiving and the receiving parameters of the echoes (such as angle of receiving, depth, etc.). For different purposes of the ultrasound echoes or different images to be generated according the ultrasound echoes, the transmitting parameters in the transmitting control sequence and the receiving parameters in the receiving control sequence may be different.

In this embodiment, the transmitting/receiving control sequence output by the transmitting/receiving sequence controller 102 to the transducer of the ultrasound probe may include a first transmitting/receiving control sequence and a second transmitting/receiving control sequence. The first transmitting/receiving control sequence may be used to obtain the ultrasound image, that is, the ultrasound transmitting parameters and receiving parameters may be determined according to the requirements of generating the ultrasound images. The first transmitting/receiving control sequence may be output before or after the transducer vibrates, so as to control the transducer to transmit the first ultrasound wave and receive the echoes of the first ultrasound wave. The second transmitting/receiving control sequence may be used to obtain the transient elasticity result in the region of interest, that is, the ultrasound transmitting parameters and receiving parameters may be determined according to the requirements for obtaining the transient elasticity result in the region of interest. For example, the parameters such as the transmitting angle of the ultrasound wave, the angle and depth of the receiving, the transmitting frequency or the like will be determined according to the region of interest selected by the user in the ultrasound image. The transmitting/receiving sequence controller 102 may output the second transmitting/receiving control sequence to the transducer after the transducer vibrates, so as to control the transducer to transmit the second ultrasound wave and receive the echoes of the second ultrasound wave.

The transmitting/receiving device 103 may be connected between the ultrasound probe and the transmitting/receiving sequence controller 102 and the echo processing device 104, and may transmit the transmitting/receiving control sequence 101*a* of the transmitting/receiving sequence controller 102 to the ultrasound probe 101 and transmit the ultrasound echo data 101*b* received by the ultrasound probe 101 to the echo processing device 104.

The echo processing device 104 may process the ultrasound echo data, such as filtering, amplifying, beam forming or other processing. The ultrasound echo data in this embodiment may include both the echo data of the second ultrasound wave for obtaining the transient elasticity and the echo data of the first ultrasound wave for generating the ultrasound image. The ultrasound image may be a B-mod image or a C-mode image, or an image formed by superimposing B-mode and C-mode images.

The data processor 105 may receive the echo data processed by the echo processing device 104, and obtain desired parameters or images using related algorithms. In one embodiments of the present disclosure, the data processor 105 may include a B-mode image processing module 1051, a C-mode image processing module 1052 and a transient elasticity processing module 1053. The B-mode image processing module 1051 may process the echo data of the first ultrasound wave output by the echo processing device 104 to generate the B-mode image data. The C-mode image processing module 1052 may process the echo data of the first ultrasound wave output by the echo processing device 104 to generate the C-mode image data. The transient elasticity processing module 1053 may process the echo data of the second ultrasound wave output by the echo processing device 104 to calculate the transient elasticity result in the region of interest.

The human-computer interaction device 107 may serve as an interaction interface between the user and the ultrasound transient elasticity measurement device 100. In one embodiment, the human-computer interaction device 107 may include a display 1071 and an input device 1072. The input device 1072 may be, for example, a keyboard or an operation button, a mouse, a trackball, or the like, and may also be a touch screen integrated with the display 1071. When the input device 1072 is a keyboard or an operation button, the user can directly input the operation information or the operation instruction through the input device. When the input device 1072 is a mouse, a trackball or a touch screen, the user may input the operation information or the operation instruction through the input device in conjunction with soft keys, operation icons, menus or the like on the display interface. Alternatively, the user may achieve the input of the operation information by the marking or the framing on the display interface. The operation instruction may be an instruction to enter the mode for obtaining the ultrasound image or an instruction to enter the mode for performing the transient elasticity detection, or an instruction to enter the mode for simultaneously obtaining the transient elasticity result and the ultrasound image. In one embodiment, the display 1071 and the input device 1072 may cooperate to achieve the selection of the region of interest. For example, the display 1071 may display the ultrasound images on the display interface, and the input device 1072 may select the region of interest on the ultrasound images according to the user's operation.

In addition, the display 1071 may also display the transient elasticity result. In this embodiment, the display 1071 may simultaneously display the ultrasound image and the transient elasticity result on the display interface. Alternatively, in one embodiment, after the transient elasticity result is obtained, the display 1071 may only display the transient elasticity result instead of displaying the ultrasound image. The transient elasticity result may be displayed on the display interface in at least one of a number, a gray bar, a color bar and a pie chart, etc.

The controller 106 may be connected with the vibrator 1012, the transmitting/receiving sequence controller 102 and the human-computer interaction device 107, and may be configured to receive the instruction at least including a transient elasticity detection instruction input by the user from the human-computer interaction device, control the vibrator to drive the transducer to vibrate, and control the output sequence of the transmitting/receiving sequence controller.

Figure 3:
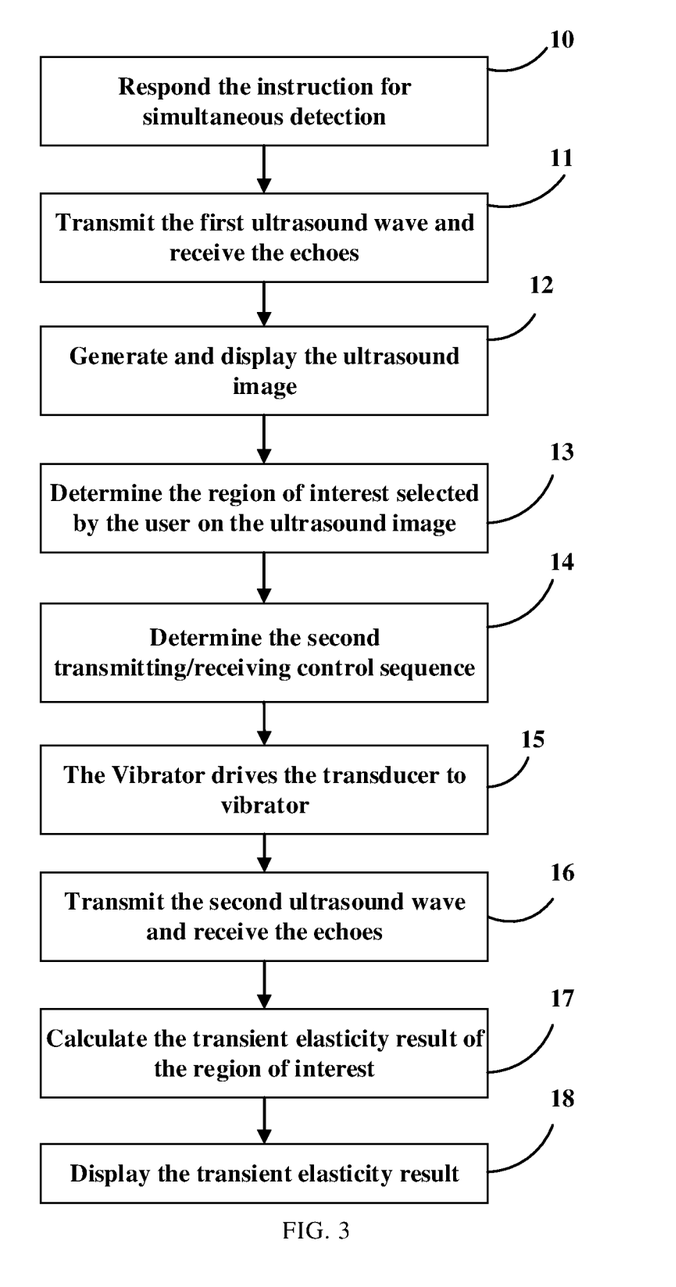
FIG. 3 is a flow chart for performing the transient elasticity detection in one embodiment.

FIG. 3 shows a measurement process of the transient elasticity measurement device in the present embodiment, which may include the following steps.

In step 10, when it is desired to simultaneously obtain the ultrasound image and the transient elasticity result, the user may input a simultaneous detection instruction through the input device. In response to the simultaneous detection instruction, the transient elasticity measurement device may enter the mode of simultaneously obtaining the ultrasound image and the transient elasticity result.

In step 11, in response to the simultaneous detection instruction, the controller may control the transmitting/receiving sequence controller to output the first transmitting/receiving control sequence to the ultrasound probe, and the ultrasound probe may transmit the first ultrasound wave and receive the echoes of the first ultrasound wave according to the first transmitting/receiving control sequence.

Figure 2:
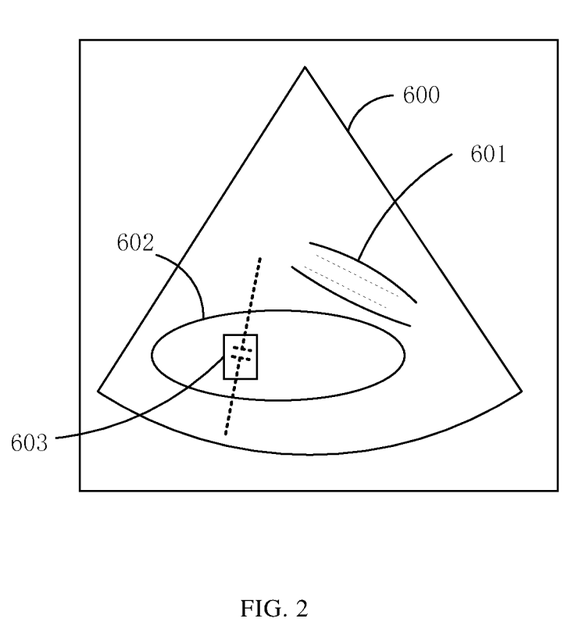
FIG. 2 is a schematic diagram of the B-mode image in one embodiment.

In step 12, the ultrasound image may be generated according to the echo data of the first ultrasound wave, and be displayed. The ultrasound image may include a B-mode image or C-mode image, or an image formed by superimposing a B-mode image and a C-mode image. The C-mode image may be a color image representing the blood flow, by which the blood flow may be observed. The B-mode image may be an image representing the anatomical structure of the tissue, and is usually shown in grayscale or in pseudo-color. The B-mode image can be used to observe the tissue, such as to observe whether the tissue has lesions or observe the location of the blood vessels. The image formed by superimposing the B-mode image and the C-mode image is an image obtained by combining the B-mode image and the C-mode image after the structures in the B-mode image are strictly corresponded in physical location to the blood flow in the C-mode image, for example, such that the blood flow in the figure is just inside the blood vessel area. Through the image formed by superimposing the B-mode image and the C-mode image, the location of the blood vessels may also be determined. The field of view of the ultrasound image may be in various shapes dependent on the probe type. For example, a linear array probe corresponds to a rectangular image, a convex array probe corresponds to a convex image, and a phased array probe corresponds to a fan-shaped image, etc. In this embodiment, a fan-shaped B-mode image is taken as an example for description, as shown in FIG. 2. In the B-mode image 600, if the doctor desires to detect the transient elasticity of the tissue 601, since according to the B-mode image 600 there is a blood vessel 601 at the upper right of the tissue 602 and the shear wave cannot pass through the liquid, the region of interest may be set selectively according to B-mode image.

In step 13, the region of interest selected by the user on the ultrasound image may be obtained. In this embodiment, the user may be allowed to mark the region of interest on the B-mode image, as shown in FIG. 2. In one example, when the ultrasound image is displayed on the display interface, an editable selection box 603 may be simultaneously displayed on the ultrasound image. The height, width and position of the selection box 603 may be adjusted by the user through the mouse, touch screen, etc. The region in the selection box 603 may be the region of interest. When the user finishes the adjustment to the size and position of the selection box 603, the region of interest is determined. In another example, the user may draw the selection box 603 on the B-mode image through the input device such as the mouse or the touch screen, etc. to determine the region of interest.

In step 14, the transmitting/receiving sequence controller may determine the second transmitting/receiving control sequence according to the region of interest. For example, the display 1071 may transmit the coordinate information of the region of interest selected by the user to the data processor 105. The data processor 105 may determine the position of the region of interest in the tissue according to the coordinate information of the region of interest. In one embodiment, the region of interest may also be selected in other ways. For example, by default, a region in a predetermined distance below a certain position of the ultrasound probe may be determined as the region of interest. According to the displayed ultrasound image, the user can move the ultrasound probe to adjust the region of interest, thereby changing the position where the transient elasticity measurement will be performed.

In step 15, the vibrator may drive the transducer to vibrate. When the region of interest is determined, the controller may output a vibration control sequence to the vibrator, and the vibrator may drive the transducer to vibrate according to the vibration control sequence. The vibration control sequence may set the parameters such as vibration waveform, vibration frequency, amplitude, vibration duration or the like. The vibration waveform may be a sine wave, a square wave, a triangle wave or the like.

In step 16, after the transducer begins to vibrates, the transmitting/receiving sequence controller may output the second transmitting/receiving control sequence to the transducer to control the transducer to transmit the second ultrasound wave to the region of interest and receive the echoes of the second ultrasound wave. In order to detect the shear wave, the ultrasound probe may be desired to transmit the ultrasound waves into the tissue and receive the echo signals for a period of time.

In steps 15 and 16, when do the transducer vibrates and transmits the second ultrasound wave may be automatically determined by the device. For example, the output timing of the vibration control sequence and the transmitting/receiving control sequence may be controlled by the controller such that the vibration control sequence and the transmitting/receiving control sequence cooperate with each other. For example, the controller may control the transmitting/receiving sequence controller to output the second transmitting/receiving control sequence to the transducer after outputting the vibration control sequence to the vibrator, or control the vibration control sequence and the second transmitting/receiving control sequence to be output simultaneously. In addition, it is also possible to manually control when the transducer vibrates and transmits the second ultrasound wave. For example, after determining the region of interest, the user may start the vibration and the transmitting of the second ultrasound wave through a control switch on the device or the ultrasound probe.

In step 17, the transient elasticity imaging module may calculate the transient elasticity result in the region of interest according to the echo data of the second ultrasound wave. The transient elasticity result may be a shear wave elasticity parameter, such as the shear wave propagation velocity, the Young's modulus and/or the shear modulus value. The transient elasticity result may also be the shear wave trajectory. For example, the transient elasticity result may be calculated by the following method.

The transient elasticity imaging module may calculate the displacement of a certain point on the shear wave propagation path according to the received echo signals. When the displacement of this point is the largest, it may be considered that the shear wave has reached this point. The propagation path or trajectory of the shear wave may be determined by the times when the shear wave reaches the points. Thereby, the shear wave trajectory may be drawn. According to the shear wave trajectory, the slopes at the points on the propagation path of the shear wave may be obtained. The slope may represent the propagation velocity of the shear wave.

For an isotropic elastomer, the shear wave propagation velocity has the following approximate relationship with the Young's modulus and the shear modulus:

$$E=3\rho c^2=3G$$

Where c represents the shear wave velocity, $\rho$ represents the tissue density, E represents the Young's modulus of the tissue, and G represents the shear modulus of the tissue. Normally, the value of $\rho$ may be the value of the density of water. Therefore, when the shear wave propagation velocity is obtained, other elasticity related parameters, such as the Young's modulus or the shear modulus, may be calculated.

Figure 4A:
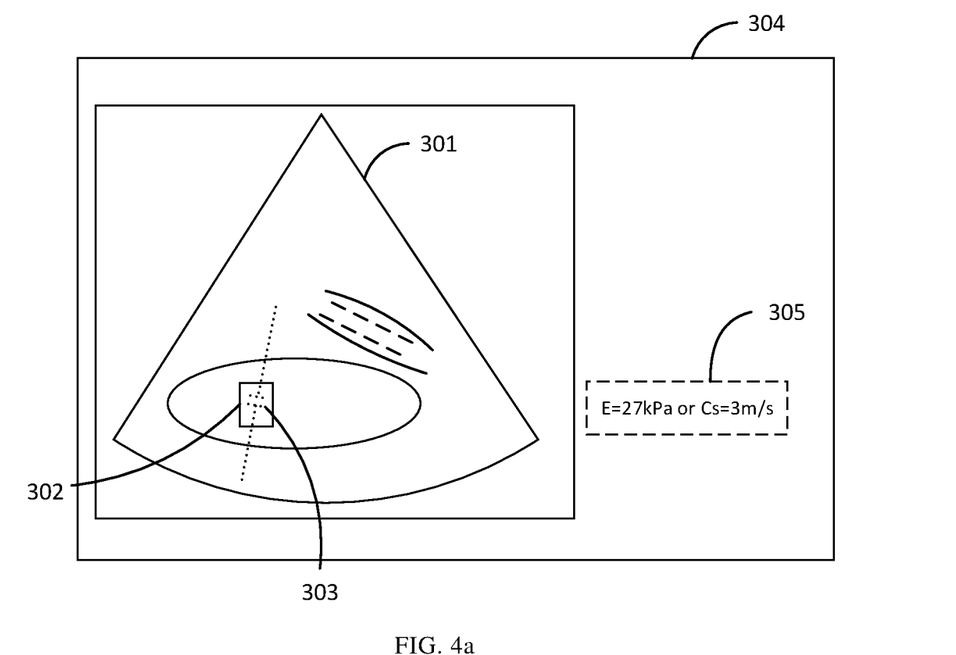
FIGS. 4a, 4b, 4c and 4d are schematic diagrams of simultaneously displaying the ultrasound image and the transient elasticity result on the display interface.
Figure 4B:
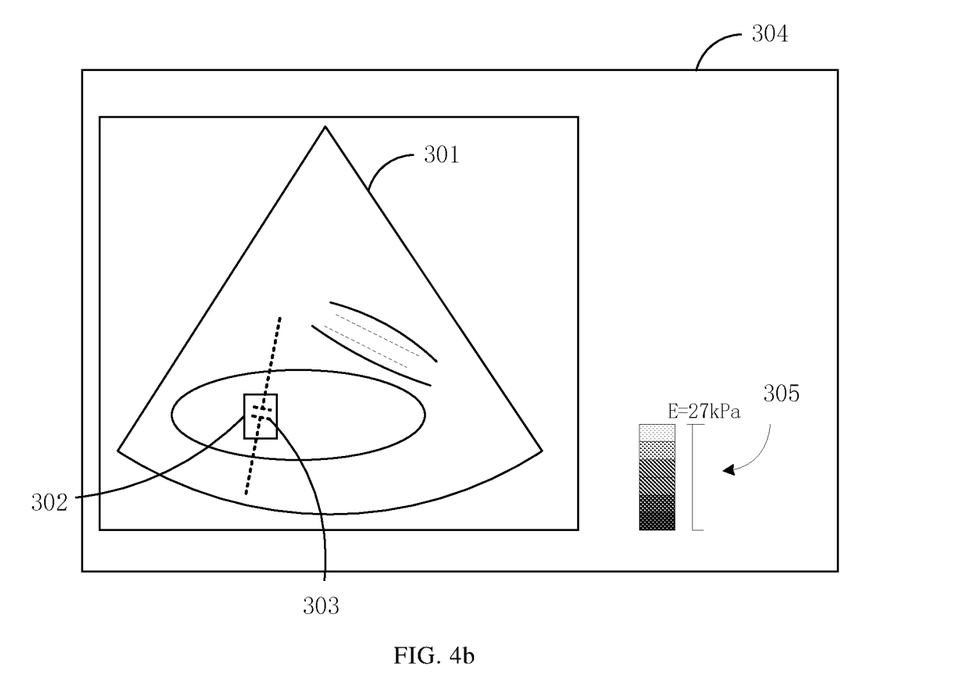
Figure 4C:
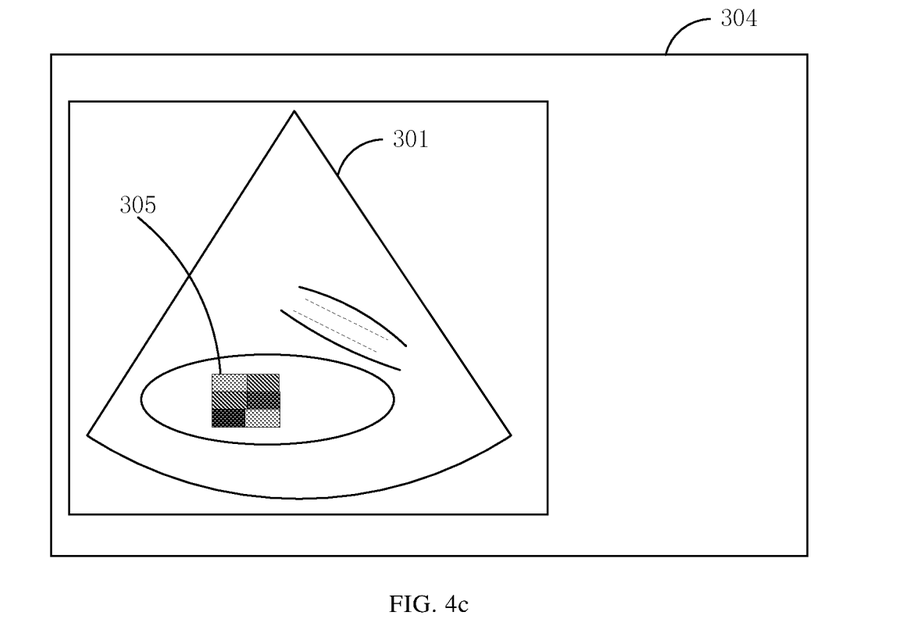

In step 18, the transient elasticity result may be displayed. For example, the display may simultaneously display the ultrasound image and the transient elasticity result on the display interface. As shown in FIGS. 4a, 4b and 4c, the ultrasound image 301 may be displayed on the display interface 304, and the selection box 302 may be displayed on the ultrasound image 301 to indicate the region of interest selected by the user. A sampling gate 303 may also be displayed. An elasticity display area 305 may be arranged beside the ultrasound image. In the elasticity display area 305, the transient elasticity measurement value at a certain position in the region of interest may be displayed. The elasticity measurement value may be presented in various ways. In FIG. 4a, the transient elasticity result is presented in number, such as E=27 kPa or Cs=3 m/s. In FIG. 4b, the transient elasticity result is presented with colors or color bar. For example, a scaled color bar may be displayed in the elasticity display area to show the quantitative analysis of the hardness change of the region of interest in the measurement depth direction. The region of interest may be represented by a box, so as to represent the transient elasticity measurement value in the box. The transient elasticity measurement value corresponding to the entire box may be represented by the statics, such as the mean, mean square deviation or variance, etc., of the elasticity measurement values at the points in the box, as shown in FIG. 4c.

Figure 4D:
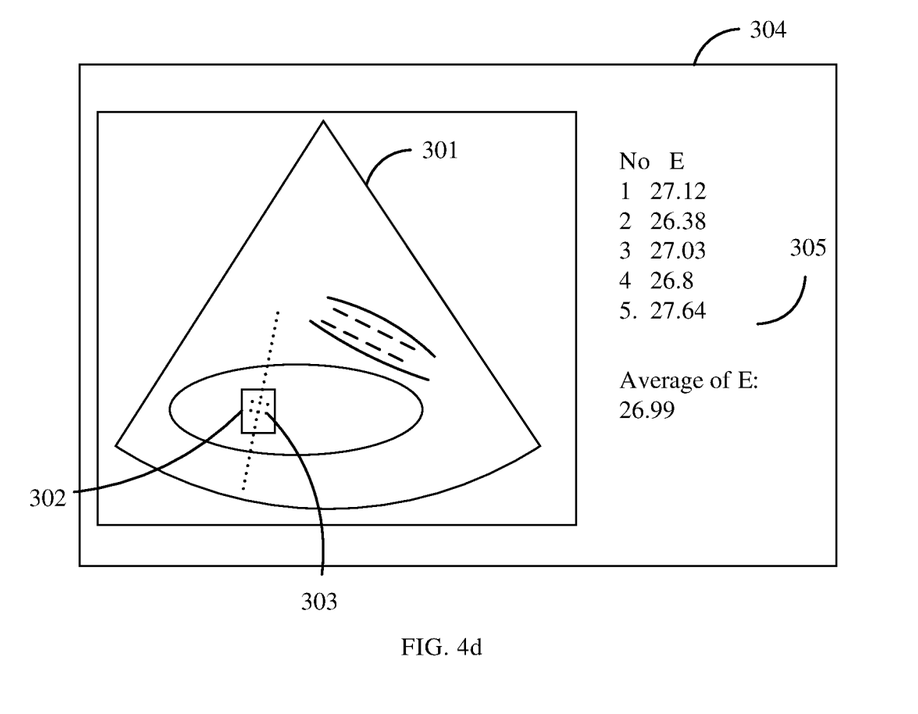

In another embodiment, the vibrator may periodically vibrate in the mode of simultaneously obtaining the transient elasticity result and the ultrasound image. For the vibrations of the vibrator, the transmitting/receiving sequence controller may periodically output the first transmitting/receiving control sequence and the second transmitting/receiving control sequence to the transducer. The display may display the real-time ultrasound images and the transient elasticity results on the display interface. In the elasticity display area 305, the transient elasticity result for each vibration. Alternatively, the average value, standard deviation or median, etc. of multiple transient elasticity results may be displayed in the elasticity display area 305, as shown in FIG. 4d. The displayed transient elasticity result may be the Young's modulus E, the shear modulus G, the shear wave propagation velocity Cs, or other parameters representing the elasticity that are calculated based on these results.

Figure 5:
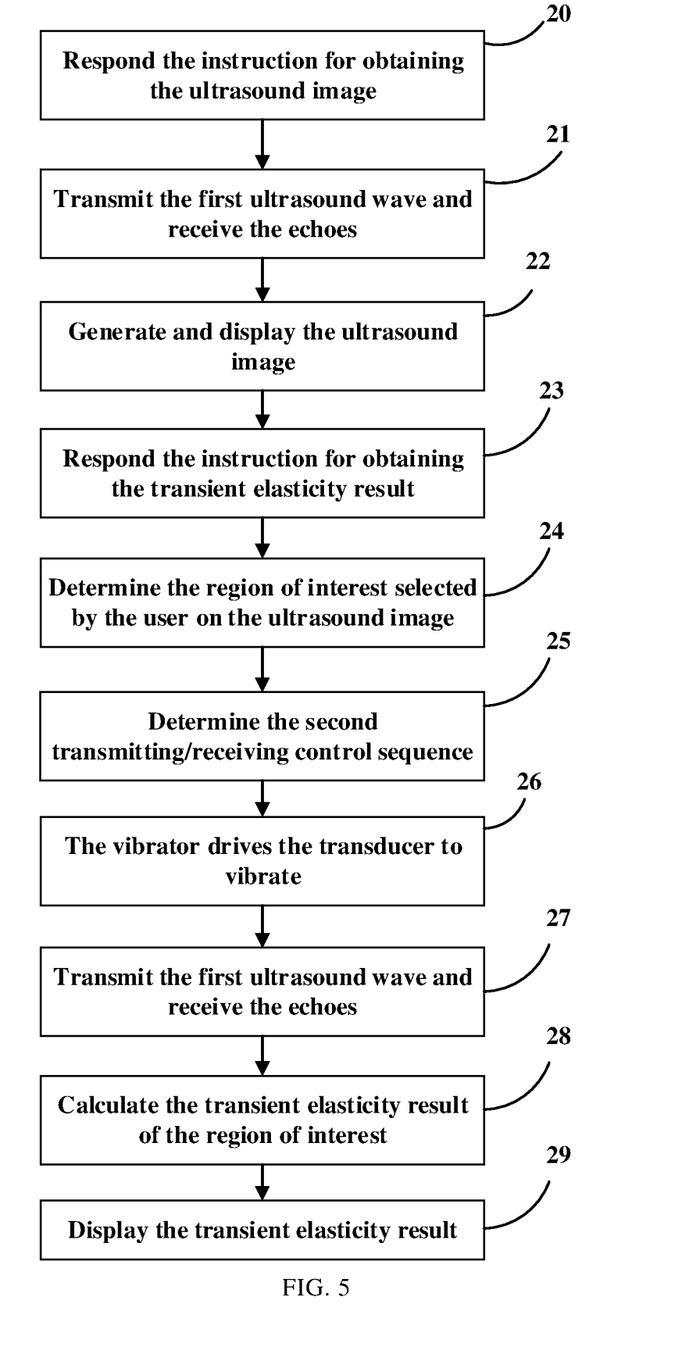
FIG. 5 is a flow chart for performing the transient elasticity detection in another embodiment.

FIG. 5 shows another measurement process using the transient elasticity measurement device of the embodiments, which may include the following steps:

In step 20, when the user desires to simultaneously obtain the ultrasound image and the transient elasticity result, the user may input an instruction for obtaining the ultrasound image through the input device. In response to this instruction, the transient elasticity measurement device may enter the mode for obtaining the ultrasound image.

In step 21, the controller may control the transmitting/receiving sequence controller to output the first transmitting/receiving control sequence to the ultrasound probe, and the ultrasound probe may transmit the first ultrasound wave and receive the echoes of the first ultrasound wave according to the first transmitting/receiving control sequence.

In step 22, the ultrasound image may be generated according to the echo data of the first ultrasound wave, and be displayed.

In step 23, the instruction for obtaining the transient elasticity result input by the user through the input device may be received. In response to this instruction, the transient elasticity measurement device may enter the mode for obtaining the transient elasticity result.

In step 24, the region of interest selected by the user on the ultrasound image may be obtained.

In step 25, the transmitting/receiving sequence controller may determine the second transmitting/receiving control sequence according to the region of interest.

In step 26, the vibrator may drive the transducer to vibrate.

In step 27, after the transducer begins to vibrate, the transmitting/receiving sequence controller may output the second transmitting/receiving control sequence to the transducer to control the transducer to transmit the second ultrasound wave to the region of interest and receive the echoes of the second ultrasound wave.

In step 28, the transient elasticity imaging module may calculate the transient elasticity result of the region of interest according to the echo data of the second ultrasound wave.

In step 29, the ultrasound image and the transient elasticity result may be displayed on the display interface.

In this embodiment, before the transient elasticity detection is performed, the ultrasound image may be generated first. Therefore, the user can observe where the tissue is diseased and where there are blood vessels through the ultrasound image, and when performing the transient elasticity measurement, the region of interest can be selected thereby so as to avoid the path with blood vessels and improve the accuracy of the transient elasticity result.

Because the vibration of the probe is involved, if the probe did not contact the tissue well, it is easy to occur that the probe leaves the tissue surface during the vibration. Moreover, pressing too tightly or too loosely may affect the accuracy of transient elasticity measurement. Therefore, generally, in the transient elasticity measurement, the user is desired to press the probe and tissue to an appropriate force range before starting the vibration and the elasticity measurement. Therefore, in one embodiment, before the transient elasticity detection is performed, the pressing pressure of the ultrasound probe on the tissue may be detected.

Figure 6:
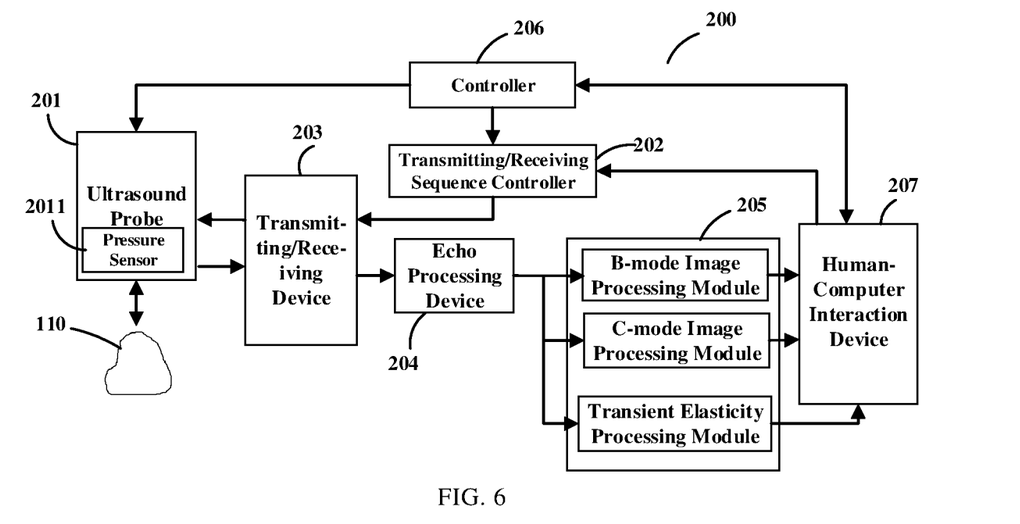
FIG. 6 is a schematic block diagram of an ultrasound transient elasticity measurement device in another embodiment.

Referring to FIG. 6, the ultrasound transient elasticity measurement device 200 may include an ultrasound probe 201, a transmitting/receiving sequence controller 202, a transmitting/receiving device 203, an echo processing device 204, a data processor 205, a human-computer interaction device 207 and a controller 206. The ultrasound probe 201 may also include a pressure sensor 2011. The output end of the pressure sensor may be connected to the controller, and may feed the sensed pressure and vibration intensity of the ultrasound probe to the biological tissue to the controller. The controller may control the vibrator to drive the transducer to vibrate when the pressure is within a predetermined range.

Figure 7:
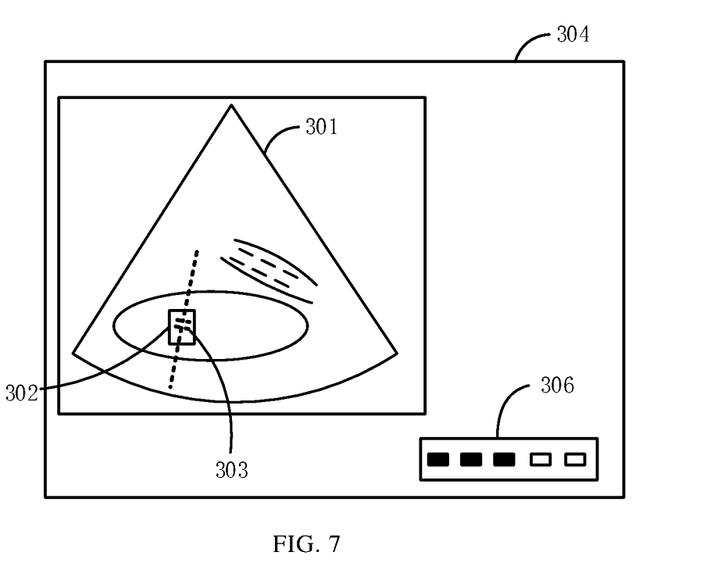
FIG. 7 is a schematic diagram showing the pressure of the ultrasound probe in one embodiment.

During the detection, before the vibrator drives the transducer to vibrate, the controller may compare the pressure detected by the pressure sensor with a predetermined range to determine whether the pressure is within the predetermined range. In one embodiment, a number, an indicator light, a gray bar or color bar or the like may be used to present the pressure to indicate whether the pressure meets the requirements of the operating specifications. As shown in FIG. 7, for example, a 5-level display box 306 may be displayed on the display interface to indicate the pressing force of the probe. The more the green bars, the greater the pressure. For example, the system may specify that the 2-4 green bars are preferred. 0 green bar, 1 green bar and 5 green bar indicate that the pressure does not meet the operating specification. When the pressure of the probe is within the predetermined range and meets the operating specification, the device may start the transient elasticity detection.

In one embodiment, the detection results of the pressure sensor may also represent the shape and amplitude of the actual vibration waveform. Since the purpose of vibration is to generate the shear waves propagating from the surface into the tissue, the shape and amplitude of the vibration waveform can also represent in a certain extent the quality of the vibration. Therefore, the quality of the vibration affects the quality of the shear wave, which may be used to determine whether the current elasticity measurement result is credible.

In other embodiments, the ultrasound transient elasticity measurement device may not use the controller to control the output timing of the vibration control sequence and the transmitting/receiving control sequence, but connect the transmitting/receiving sequence controller and the vibrator. When it is detected that the vibrator is vibrating, the transmitting/receiving sequence controller may output the second transmitting/receiving control sequence.

The functions in the present disclosure may be implemented by the program described in the embodiments above or by hardware, such as by an application specific integrated circuit built by gate circuits. Those skilled in the art can understand that the various programs in the embodiments above may be stored in a computer-readable storage medium. The storage medium may include a read-only memory, a random access memory, a magnetic disk or an optical disk, etc. The data processor may achieve the functions above by executing the programs.

This disclosure has been made with reference to various exemplary embodiments. However, those skilled in the art will recognize that changes and modifications may be made to the exemplary embodiments without departing from the scope of the present disclosure. For example, various operational steps, as well as components for carrying out operational steps, may be implemented in alternate ways depending upon the particular application or in consideration of any number of cost functions associated with the operation of the system, e.g., one or more of the steps may be deleted, modified, or combined with other steps.

Additionally, as will be appreciated by one of ordinary skill in the art, principles of the present disclosure may be reflected in a computer program product on a computer-readable storage medium having computer-readable program code means embodied in the storage medium. Any tangible, non-transitory computer-readable storage medium may be utilized, including magnetic storage devices (hard disks, floppy disks, and the like), optical storage devices (CD-ROMs, DVDs, Blu-Ray discs, and the like), flash memory, and/or the like. These computer program instructions may be loaded onto a general purpose computer, special purpose computer, or other programmable data processing apparatus to produce a machine, such that the instructions that execute on the computer or other programmable data processing apparatus create means for implementing the functions specified. These computer program instructions may also be stored in a computer-readable memory that can direct a computer or other programmable data processing apparatus to function in a particular manner, such that the instructions stored in the computer-readable memory produce an article of manufacture, including implementing means that implement the function specified. The computer program instructions may also be loaded onto a computer or other programmable data processing apparatus to cause a series of operational steps to be performed on the computer or other programmable apparatus to produce a computer-implemented process, such that the instructions that execute on the computer or other programmable apparatus provide steps for implementing the functions specified.

While the principles of this disclosure have been shown in various embodiments, many modifications of structure, arrangements, proportions, elements, materials, and components, which are particularly adapted for a specific environment and operating requirements, may be used without departing from the principles and scope of this disclosure. These and other changes or modifications are intended to be included within the scope of the present disclosure.

The foregoing specification has been described with reference to various embodiments. However, one of ordinary skill in the art will appreciate that various modifications and changes can be made without departing from the scope of the present disclosure. Accordingly, this disclosure is to be regarded in an illustrative rather than a restrictive sense, and all such modifications are intended to be included within the scope thereof. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, a required, or an essential feature or element. As used herein, the terms "comprises," "comprising," and any other variation thereof, are intended to cover a non-exclusive inclusion, such that a process, a method, an article, or an apparatus that comprises a list of elements does not include only those elements but may include other elements not expressly listed or inherent to such process, method, system, article, or apparatus. Also, as used herein, the terms "coupled," "coupling," and any other variation thereof are intended to cover a physical connection, an electrical connection, a magnetic connection, an optical connection, a communicative connection, a functional connection, and/or any other connection.

Those having skill in the art will appreciate that many changes may be made to the details of the above-described embodiments without departing from the underlying principles of the disclosure. The scope of the present disclosure should, therefore, be determined only by the following claims.

The invention claimed is:

1. An ultrasound transient elasticity measurement device, comprising:
   an ultrasound probe comprising a vibrator and a transducer, wherein, the vibrator is configured to drive the transducer to vibrate to generate a shear wave that propagates to inside of a biological tissue that contains one or more blood vessels, the transducer comprises multiple elements, and at least part of the multiple elements are configured to transmit a first ultrasound wave to the biological tissue before the transducer vibrates and to receive echoes of the first ultrasound wave returned from the biological tissue to obtain echo data of the first ultrasound wave, and to transmit a second ultrasound wave to a region of interest in the biological tissue when the transducer vibrates and to receive echoes of the second ultrasound wave returned from the biological tissue to obtain echo data of the second ultrasound wave;
   a transmitting/receiving sequence controller configured to output a first transmitting/receiving control sequence to the transducer before the transducer vibrates to control the transducer to transmit the first ultrasound wave and to receive the echoes of the first ultrasound wave, and output a second transmitting/receiving control sequence to the transducer when the transducer vibrates to control the transducer to transmit the second ultrasound wave and to receive the echoes of the second ultrasound wave, wherein, the first transmitting/receiving control sequence is for at least obtaining an ultrasound image of the biological tissue and determining a location of the one or more blood vessels based on the ultrasound image of the biological tissue, the second transmitting/receiving control sequence is for obtaining a transient elasticity result of the region of interest within the biological tissue, the region of interest is smaller than the biological tissue and avoids the location of the one or more blood vessels, and the second transmitting/receiving control sequence is determined according to the region of interest, wherein the region of interest is determined by displaying an editable selection box on the ultrasound image and adjusting a height, width, and position of the selection box;

a data processor configured to generate ultrasound image data according to the echo data of the first ultrasound wave and to calculate the transient elasticity result of the region of interest according to the echo data of the second ultrasound wave, wherein the data processor is configured to generate the ultrasound image data by generating the ultrasound image including a B-mode image and a C-mode image, and superimposing the B-mode image and the C-mode image to generated a superimposed image, wherein superimposing the B-mode image and the C-mode image comprises corresponding structures in the B-mode image in physical locations to blood flow in the C-mode image such that the blood flow is inside the one or more blood vessels, wherein the region of interest is selected to avoid the location of the one or more blood vessels on the superimposed image;

a display configured to display the ultrasound image on a display interface according to the ultrasound image data and display the transient elasticity result; and a controller connected to the vibrator, the transmitting/receiving sequence controller and the display, and configured to receive an instruction comprising at least an instruction for obtaining the transient elasticity result from the display, to control a timing of outputting a vibration control sequence to the vibrator and a timing of outputting the second transmitting/receiving control sequence to the transducer by the transmitting/receiving sequence controller, and to control the vibration control sequence and the second transmitting/receiving control sequence to be output simultaneously, such that the vibration control sequence and the second transmitting/receiving control sequence cooperate with each other, wherein the ultrasound probe further comprises a pressure sensor connected to the controller, and the controller is further configured to determine whether the transient elasticity result is credible by using a detection result of the pressure sensor representing a shape and amplitude of an actual vibration waveform.

2. The device of claim 1, wherein the transmitting/receiving sequence controller outputs the first transmitting/receiving control sequence again when outputting the second transmitting/receiving control sequence to control the transducer to further transmit the first ultrasound wave when transmitting the second ultrasound wave.

3. The device of claim 1, wherein the display simultaneously displays the ultrasound image and the transient elasticity result on the display interface.

4. The device of claim 1, wherein, the vibrator periodically vibrates in a mode of simultaneously obtaining the transient elasticity result and the ultrasound image, the transmitting/receiving sequence controller periodically outputs the first transmitting/receiving control sequence and the second transmitting/receiving control sequence, and the display displays the ultrasound image and the transient elasticity result in in real-time.

5. The device of claim 1, wherein the display displays the transient elasticity result on the display interface in at least one of a number, a gray bar, a color bar, and a pie chart.

6. The device of claim 1, wherein an output end of the pressure sensor is connected to the controller, and the pressure sensor is configured to feed a sensed pressure of the ultrasound probe on the biological tissue to the controller.

7. The device of claim 6, wherein the controller determines whether the sensed pressure is within a predetermined range, and controls the vibrator to drive the transducer to vibrate when the sensed pressure is within the predetermined range.

8. The device of claim 6, wherein the controller controls the display to display the sensed pressure on the display interface.

9. An ultrasound transient elasticity measurement method, executed by an ultrasound transient elasticity measurement device, wherein the ultrasound transient elasticity measurement device comprises an ultrasound probe comprising a vibrator, a transducer and a pressure sensor, a transmitting/receiving sequence controller, a display and a controller, and the controller is connected to the vibrator, the transmitting/receiving sequence controller, the display and the pressure sensor, the method comprising:

outputting a first transmitting/receiving control sequence to the transducer of the ultrasound probe to control the transducer to transmit a first ultrasound wave to a biological tissue that contains one or more blood vessels and to receive echoes of the first ultrasound wave returned from the biological tissue to obtain an echo data of the first ultrasound wave, wherein the first transmitting/receiving control sequence is for at least obtaining an ultrasound image of the biological tissue and determining a location of the one or more blood vessels based on the ultrasound image of the biological tissue;

generating an ultrasound image data according to the echo data of the first ultrasound wave by generating the ultrasound image including a B-mode image and a C-mode image, and superimposing the B-mode image and the C-mode image to generate a superimposed image, wherein superimposing the B-mode image and the C-mode image comprises corresponding structures in the B-mode image in physical locations to blood flow in the C-mode image such that the blood flow is inside the one or more blood vessels;

displaying the ultrasound image of the biological tissue according to the ultrasound image data;

determining a region of interest within the biological tissue, the region of interest being smaller than the biological tissue and avoiding the location of the one or more blood vessels on the superimposed image, and the region of interest being determined by displaying an editable selection box on the ultrasound image and adjusting a height, width and position of the selection box;

generating a second transmitting/receiving control sequence according to the region of interest, wherein the second transmitting/receiving control sequence is for obtaining a transient elasticity result of the region of interest;

controlling the vibrator to drive the transducer to vibrate after the region of interest is determined;

outputting the second transmitting/receiving control sequence to the transducer when the transducer vibrates to control the transducer to transmit a second ultrasound wave to the region of interest and to receive echoes of the second ultrasound wave to obtain an echo data of the second ultrasound wave; and calculating the transient elasticity result of the region of interest according to the echo data of the second ultrasound wave;

wherein the method further comprises:

receiving, by the controller, an instruction comprising at least an instruction for obtaining the transient elasticity result from the display, controlling a timing of outputting a vibration control sequence to the vibrator and a timing of outputting the second transmitting/receiving control sequence to the transducer by the transmitting/receiving sequence controller, and controlling the vibration control sequence and the second transmitting/receiving control sequence to be output simultaneously, such that the vibration control sequence and the second transmitting/receiving control sequence cooperate with each other, and determining, by the controller, whether the transient elasticity result is credible by using a detection result of the pressure sensor representing a shape and amplitude of an actual vibration waveform.

10. The method of claim 9, further comprising: displaying the transient elasticity result on a display interface.

11. The method of claim 10, wherein the ultrasound image and the transient elasticity result are simultaneously displayed on the display interface.

12. The method of claim 9, further comprising:

controlling the vibrator periodically to vibrate in a mode of simultaneously obtaining the transient elasticity result and the ultrasound image;

periodically outputting the first transmitting/receiving control sequence and the second transmitting/receiving control sequence to the transducer; and displaying the ultrasound image and the transient elasticity result in in real-time.

13. The method of claim 10, wherein the transient elasticity result is displayed on the display interface in at least one of a number, a gray bar, a color bar, and a pie chart.

14. The method of claim 9, wherein the transient elasticity result comprises a shear wave elasticity parameter and/or a shear wave trajectory, wherein the shear wave elasticity parameter comprises at least one of a shear wave propagation velocity, a Young's modulus, and a shear modulus.

15. The method of claim 9, before controlling the vibrator to drive the transducer to vibrate, the method further comprising: receiving a pressure of the ultrasound probe on the biological tissue sensed by the pressure sensor, determining whether the pressure is within a predetermined range, and controlling the vibrator to drive the transducer to vibrate when the pressure is within the predetermined range.

* * * * *